US006806261B2

(12) United States Patent
Slusher et al.

(10) Patent No.: US 6,806,261 B2
(45) Date of Patent: Oct. 19, 2004

(54) METHODS FOR TREATING CERTAIN DISEASES USING NAALADASE INHIBITORS

(75) Inventors: Barbara S. Slusher, Kingsville, MD (US); Xi-Chun May Lu, Laurel, MD (US); Krystyna Wozniak, Bel Air, MD (US)

(73) Assignee: Guilford Pharmaceuticals Inc., Baltimore, MD (US)

( * ) Notice: Subject to any disclaimer, the term of this patent is extended or adjusted under 35 U.S.C. 154(b) by 31 days.

(21) Appl. No.: 10/209,011

(22) Filed: Aug. 1, 2002

(65) Prior Publication Data

US 2003/0017965 A1 Jan. 23, 2003

Related U.S. Application Data

(63) Continuation of application No. 09/425,197, filed on Oct. 22, 1999, now Pat. No. 6,444,657, which is a continuation-in-part of application No. 09/224,291, filed on Dec. 31, 1998, now abandoned.

(51) Int. Cl.[7] ............... A61K 31/215; A61K 31/255; A61K 31/662
(52) U.S. Cl. ............... 514/89; 514/114; 514/118; 514/119; 514/120; 514/121; 514/124; 514/513; 514/529; 514/546; 514/550; 514/551; 514/557; 514/561; 514/570; 514/574
(58) Field of Search ............... 514/89, 114, 118, 514/119, 120, 121, 124, 513, 529, 546, 550, 551, 557, 561, 570, 574

(56) References Cited

U.S. PATENT DOCUMENTS

| | | |
|---|---|---|
| 4,671,958 A | 6/1987 | Rodwell et al. ............... 514/2 |
| 4,741,900 A | 5/1988 | Alvarez et al. ............... 424/85 |
| 4,857,637 A | 8/1989 | Hammonds et al. ........ 530/403 |
| 4,867,973 A | 9/1989 | Goers et al. ............. 424/85.91 |
| 4,906,779 A | 3/1990 | Weber et al. ............... 564/238 |
| 4,918,064 A | 4/1990 | Cordi et al. ................. 514/114 |

(List continued on next page.)

FOREIGN PATENT DOCUMENTS

| | | |
|---|---|---|
| WO | WO 96/26272 | 8/1996 |
| WO | WO 97 483 99 | 12/1997 |
| WO | WO 97 484 00 | 12/1997 |

(List continued on next page.)

OTHER PUBLICATIONS

Lu, Xi–Chu et al., "Neuroprotective effect of NAALADase inhibition in rat MCAO is partially mediated through TGF–beta." Society for Neuroscience Abstracts, vol. 25, No. 1–2, pp. 2231 (Oct. 1999).

Samoilovich, E.O. et al., "The effectiveness of phosphonic acid derivatives and their combinations with intereferon inducers in cell cultures and mice with herpes meningoencephalits" Database Chemabs 'Online!' Chemical Abstracts Service, Database accession No. 111:224810 XP002139382 see m=5962–42–5 abstract & VOPR. VIRUSOL (1989, 34(4),466–74).

Shah, B. et al., "NAALADase inhibition enhances myelination in dorsal root ganglia–Schwann cell–co–cultures." Society for Neuroscience Abstracts, vol. 24, No. 1–2, pp. 1561. (Nov. 1998).

(List continued on next page.)

*Primary Examiner*—Jeffrey Edwin Russel
(74) *Attorney, Agent, or Firm*—Foley & Lardner LLP

(57) ABSTRACT

The present invention relates to methods for regulating the release of TGF-$\beta$ from living cells in vitro or in vivo, comprising bringing the cells into contact with an effective amount of a NAALADase inhibitor. Such methods are believed to be useful for affecting neuroregeneration, cell proliferation, cell differentiation, extracellular matrix formation, myelination, inflammation, immune function, liver function, pancreatic function, angiogenesis, or wound healing; and/or for preventing or treating diabetes.

18 Claims, 6 Drawing Sheets

U.S. PATENT DOCUMENTS

| | | | |
|---|---|---|---|
| 4,937,183 A | 6/1990 | Ultee et al. | 435/68.1 |
| 4,950,738 A | 8/1990 | King et al. | 530/322 |
| 4,959,493 A | 9/1990 | Ohfume et al. | 562/506 |
| 4,966,999 A | 10/1990 | Coughlin et al. | 564/150 |
| 4,994,446 A | 2/1991 | Sokolovsky et al. | 514/75 |
| 5,047,227 A | 9/1991 | Rodwell et al. | 424/1.1 |
| 5,093,525 A | 3/1992 | Weber et al. | 564/238 |
| 5,136,080 A | 8/1992 | Miller et al. | 558/410 |
| 5,140,104 A | 8/1992 | Coughlin et al. | 530/330 |
| 5,155,027 A | 10/1992 | Sledziewski et al. | 435/69.7 |
| 5,156,840 A | 10/1992 | Goers et al. | 424/85.91 |
| 5,162,504 A | 11/1992 | Horoszewicz | 530/388.2 |
| 5,162,512 A | 11/1992 | King et al. | 536/6.4 |
| 5,190,976 A | 3/1993 | Weber et al. | 514/634 |
| 5,216,126 A | 6/1993 | Cox et al. | 530/350 |
| 5,229,495 A | 7/1993 | Ichijo et al. | 530/350 |
| 5,242,915 A | 9/1993 | Ueda et al. | 514/210 |
| 5,262,568 A | 11/1993 | Weber et al. | 564/238 |
| 5,326,856 A | 7/1994 | Coughlin et al. | 534/14 |
| 5,336,689 A | 8/1994 | Weber et al. | 514/634 |
| 5,340,925 A | 8/1994 | Lioubin et al. | 530/395 |
| 5,349,066 A | 9/1994 | Kaneko et al. | 546/297 |
| 5,449,761 A | 9/1995 | Belinka, Jr. et al. | 534/10 |
| 5,453,492 A | 9/1995 | Butzow et al. | 530/413 |
| 5,474,547 A | 12/1995 | Aebischer et al. | 604/891.1 |
| 5,489,525 A | 2/1996 | Pastan | 435/7.23 |
| 5,500,420 A | 3/1996 | Maiese | 514/131 |
| 5,506,107 A | 4/1996 | Cunningham et al. | 435/7.21 |
| 5,527,885 A | 6/1996 | Coughlin et al. | 534/14 |
| 5,538,866 A | 7/1996 | Israeli et al. | 435/69.3 |
| 5,543,143 A | 8/1996 | Reed | 424/130.1 |
| 5,547,854 A | 8/1996 | Donahoe et al. | 435/69.1 |
| 5,565,439 A | 10/1996 | Piazza et al. | 514/110 |
| 5,567,584 A | 10/1996 | Sledziewski et al. | 435/6 |
| 5,578,703 A | 11/1996 | Ichijo et al. | 530/350 |
| 5,583,153 A * | 12/1996 | Brahn | 514/449 |
| 5,614,502 A * | 3/1997 | Flotte et al. | 514/34 |
| 5,616,561 A | 4/1997 | Barcellos-Hoff | 514/13 |
| 5,662,904 A | 9/1997 | Ferguson et al. | 424/130.1 |
| 5,672,592 A | 9/1997 | Jackson et al. | 514/75 |
| 5,693,607 A | 12/1997 | Segarini et al. | 514/2 |
| 5,698,402 A | 12/1997 | Luderer et al. | 435/7.4 |
| 5,707,974 A * | 1/1998 | Kennedy | 514/56 |
| 5,795,877 A | 8/1998 | Jackson et al. | 514/75 |
| 5,804,602 A | 9/1998 | Slusher et al. | 514/574 |
| 5,824,662 A | 10/1998 | Slusher et al. | 514/75 |
| 5,863,536 A | 1/1999 | Jackson et al. | 424/130.1 |
| 5,880,112 A | 3/1999 | Jackson et al. | 514/121 |
| 5,902,817 A | 5/1999 | Jackson et al. | 514/347 |
| 5,962,521 A | 10/1999 | Jackson et al. | 514/530 |
| 5,968,915 A | 10/1999 | Jackson et al. | 514/89 |
| 5,977,090 A | 11/1999 | Slusher et al. | 514/143 |
| 5,981,209 A | 11/1999 | Slusher et al. | 435/23 |
| 5,985,855 A | 11/1999 | Slusher et al. | 514/75 |
| 6,004,946 A | 12/1999 | Slusher et al. | 514/75 |
| 6,011,021 A | 1/2000 | Slusher et al. | 514/75 |
| 6,017,903 A | 1/2000 | Slusher et al. | 514/75 |
| 6,025,344 A | 2/2000 | Jackson et al. | 514/75 |
| 6,025,345 A | 2/2000 | Jackson et al. | 514/75 |
| 6,028,216 A | 2/2000 | Morales et al. | 562/24 |
| 6,046,180 A | 4/2000 | Jackson et al. | 514/75 |
| 6,054,444 A | 4/2000 | Jackson et al. | 514/89 |
| 6,071,965 A | 6/2000 | Jackson et al. | 514/75 |
| 6,121,252 A | 9/2000 | Jackson et al. | 514/89 |
| 6,228,888 B1 | 5/2001 | Slusher | 514/574 |
| 6,271,245 B1 | 8/2001 | Jackson et al. | 514/346 |
| 6,288,046 B1 | 9/2001 | Jackson et al. | 514/120 |
| 6,313,159 B1 | 11/2001 | Jackson et al. | 514/423 |
| 6,358,741 B1 * | 3/2002 | Schmidt et al. | 435/455 |
| 6,395,718 B1 * | 5/2002 | Slusher et al. | 514/75 |
| 6,444,657 B1 * | 9/2002 | Slusher et al. | 514/120 |

FOREIGN PATENT DOCUMENTS

| | | |
|---|---|---|
| WO | WO 97/48409 | 12/1997 |
| WO | WO 98 130 46 | 4/1998 |
| WO | WO 98 452 56 | 10/1998 |
| WO | WO 98 452 57 | 10/1998 |
| WO | WO 98 479 06 | 10/1998 |
| WO | WO 98 538 12 | 12/1998 |
| WO | WO 99 085 21 | 2/1999 |
| WO | WO 99 338 47 | 7/1999 |
| WO | WO 99 338 49 | 7/1999 |
| WO | WO 99 502 72 | 10/1999 |
| WO | WO 00 016 68 | 1/2000 |

OTHER PUBLICATIONS

Thomas, Ajit G. et al, "The role of TGF–beta in the neuroprotection medicated by NAALADase inhibition in cortical cell cultures." Society for Neuroscience Abstracts, vol. 25, No. 1–2, pp. 2231 (Oct. 1999).

Yao, Y.–M. et al., "Inhibition of NAALADase activity promoted myelin formation following mouse sciatic nerve cryolesion." Society for Neuroscience Abstracts, vol. 23, No. 1–2, pp. 2302 (Oct. 1997).

Yao, Y.–M. et al., "NAALADase inhibition enhances myelination following sciatic nerve cryolesion and tellurium intoxication." Society for Neuroscience Abstracts, vol. 24, No. 1–2, pp. 1755 (Nov. 1998).

International Search Report in PCT/US99/31039 (Jun. 23, 2000).

Written Opinion in PCT/US99/31039 (Oct. 4, 2000).

Wroblewska, B. et al., "N–Acetylaspartylglutamate Selectively Activates mGluR3 Receptors in Transfected Cells," *J. Neurochem.*, 69(1), 174–181, (1997).

Hayashi, Hidetoshi et al., "The MAD–Related Protein SMAD7 Associates with the TGFβ Receptor and Functions as an Antagonist of TGFβ Signaling", *Cell*, vol. 89, pp. 1165–1173 (Jun. 27, 1997).

Nakao, Atsuhito et al., "Identification of Smad 7, a TGFβ–inducible antagonsit of TGF–β signalling", *Nature*, vol. 389, pp. 631–635 (Oct. 9, 1997).

Rothstein, Jeffrey D. et al., "Abnormal Excitatory Amino Acid Metabolism in Amyotrophic Lateral Sclerosis", *Annals. of Neurology*, vol. 28, No. 1, pp. 18–25 (Jul. 1990).

Coyle, J.T. et al., "N–Acetyl–aspartyl Glutamate Recent Developments", *Excitatory Amino Acids*, pp. 69–77 (1990).

Tsai, Guochuan et al., "Reductions in acidic amino acids and N–acetylaspartylglutamate in amyotrophic lateral sclerosis CNS", *Brain Research*, vol. 556, pp. 151–156 (1991).

Meyerhoff, James L. et al., "Genetically epilepsy–prone rats have increased brain regional activity of an enzyme which liberates glutamate from N–acetyl–aspartyl–glutamate", *Brain Research*, vol. 593, pp. 140–143 (1992).

Meyerhoff, James L. et al., "Activity of a NAAG–hydrolyzing enzyme in brain may affect seizure susceptibility in genetically epilepsy–prone rats", *Molecular Neurobiology of Epilepsy*, pp. 163–172 (1992).

Slusher, Barbara Stauch, "NAALADase: A Potential Regulator of Synaptic Glutamate", *Biotech Update DuPont NEN*, 9:2, pp. 37–39 (1994).

Jackson, Paul F. et al., "Design, Synthesis, and Biological Activity of a Potent Inhibitor of the Neuropeptidase N–Acetylated α–Linked Acidic Dipeptidase", *J. of Medicinal Chemistry*, (1995).

Vornov, James J., "Toxic NMDA–Receptor Activation Occurs During Recovery in a Tissue Culture Model of Ischemia", *J. of Neurochemistry*, 65, p. 1681–1691 (1995).

Woods, D. et al., "Gender–linked injury after focal cerebral ischemia," *Soc. For Neuroscience 1996 Abstract Form*, (1996).

Bhardwaj, A. et al., "Striatal nitric oxide (NO) production is enhanced in focal cerebral ischemia: An in vivo microdialysis study," *Soc. For Neuroscience 1996 Abstract Form*, (1996).

Carter, R. et al., "Prostate–specific membrane antigen is a hydrolase with substrate and pharmacologic characteristics of neuropeptidase," *Proc. Nat. Acad. Sci.*, 93, p. 749–753 (1996).

* cited by examiner

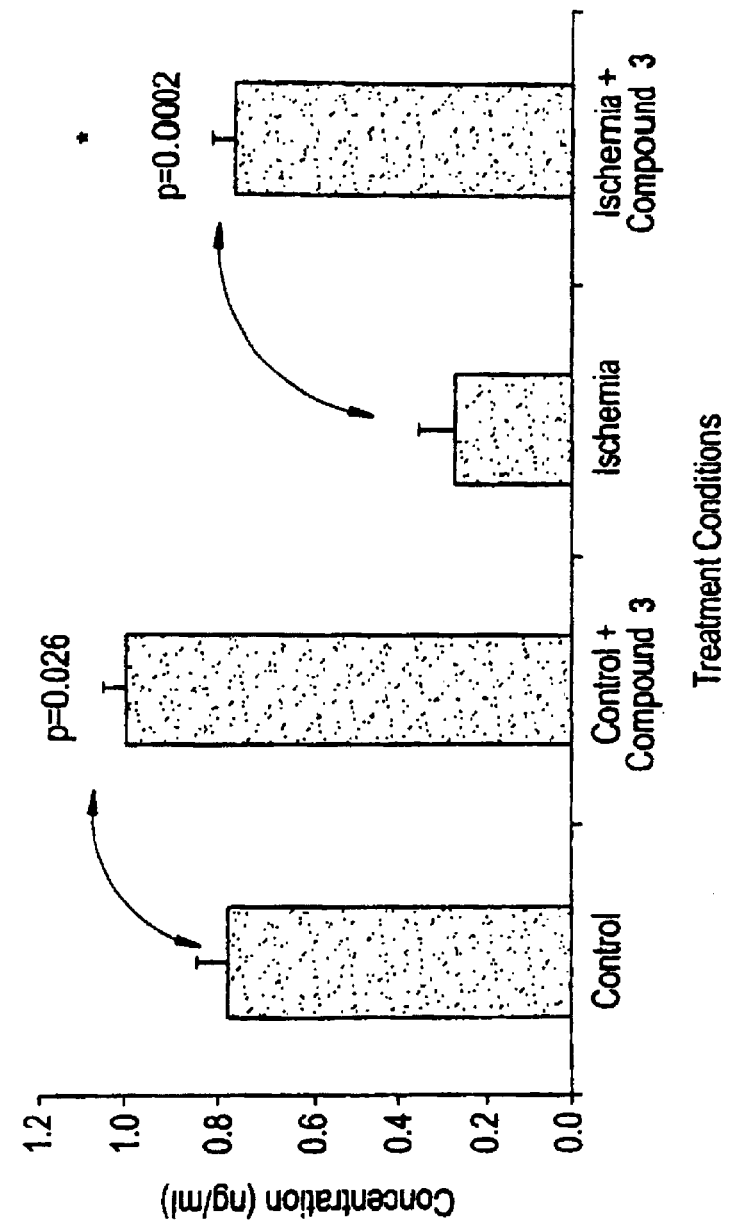

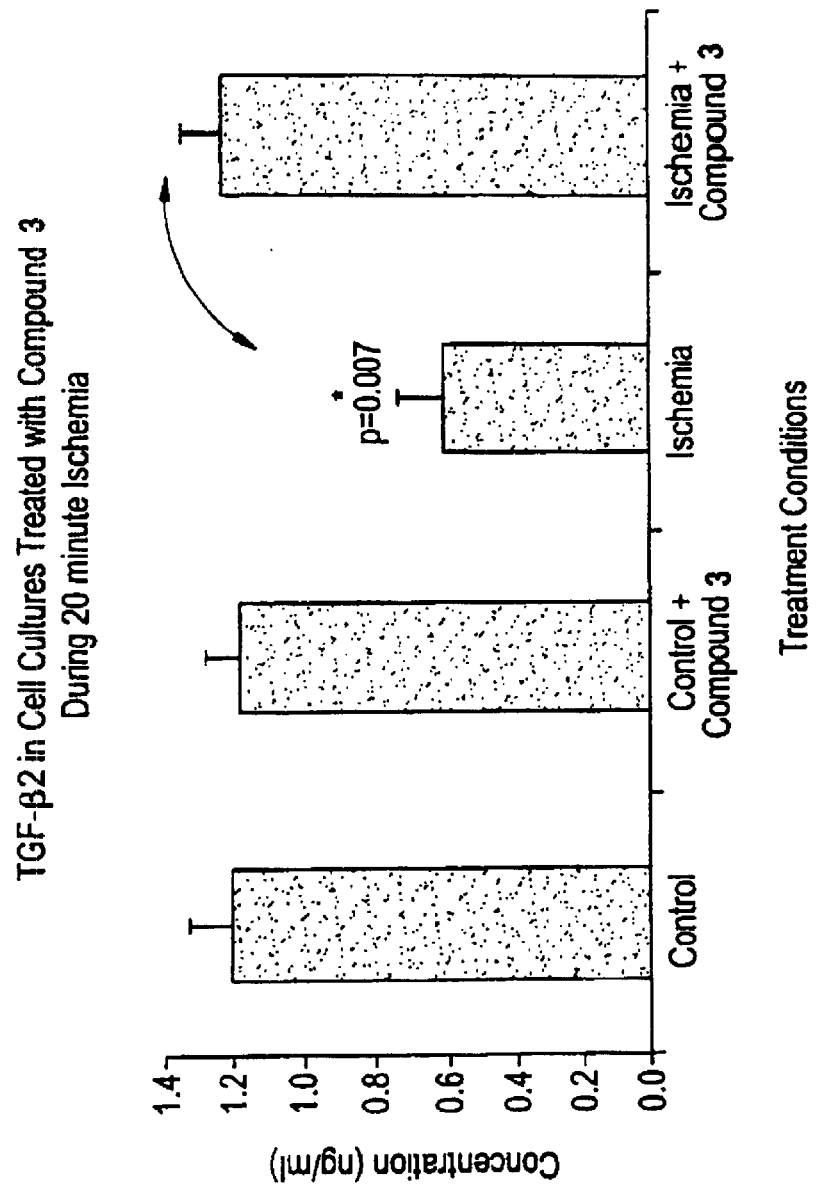

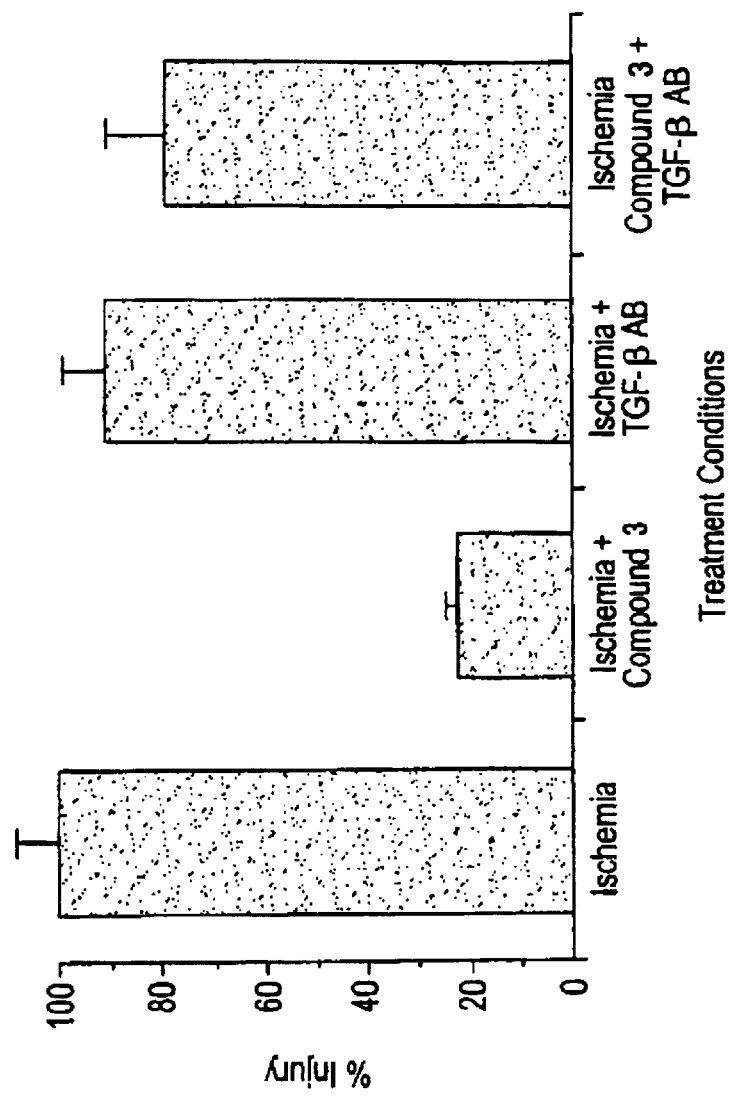

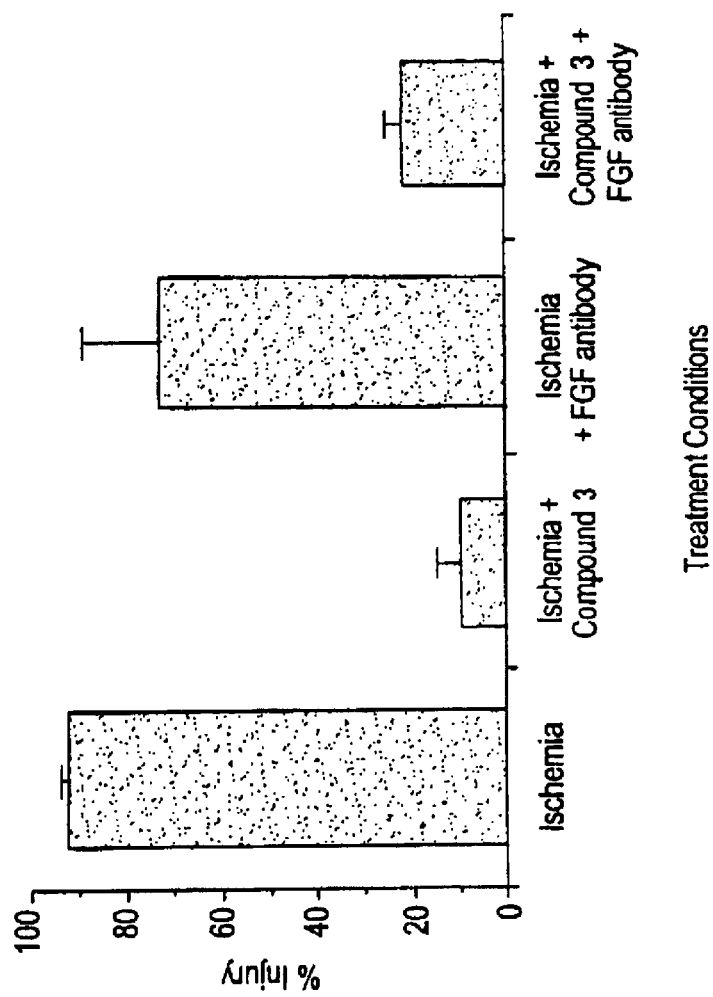

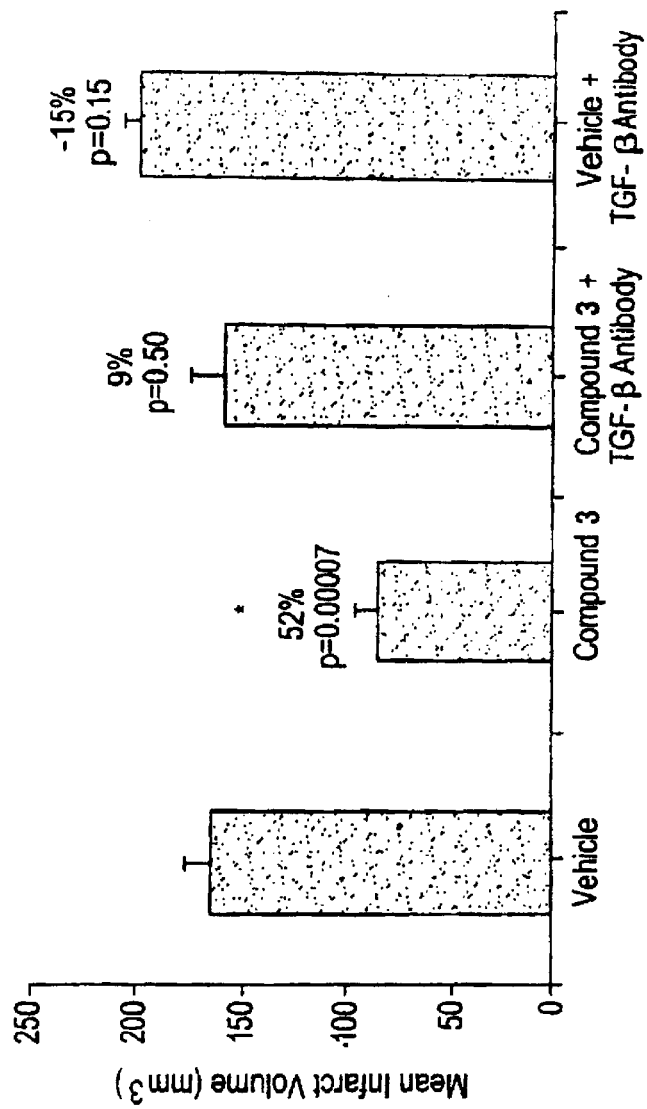

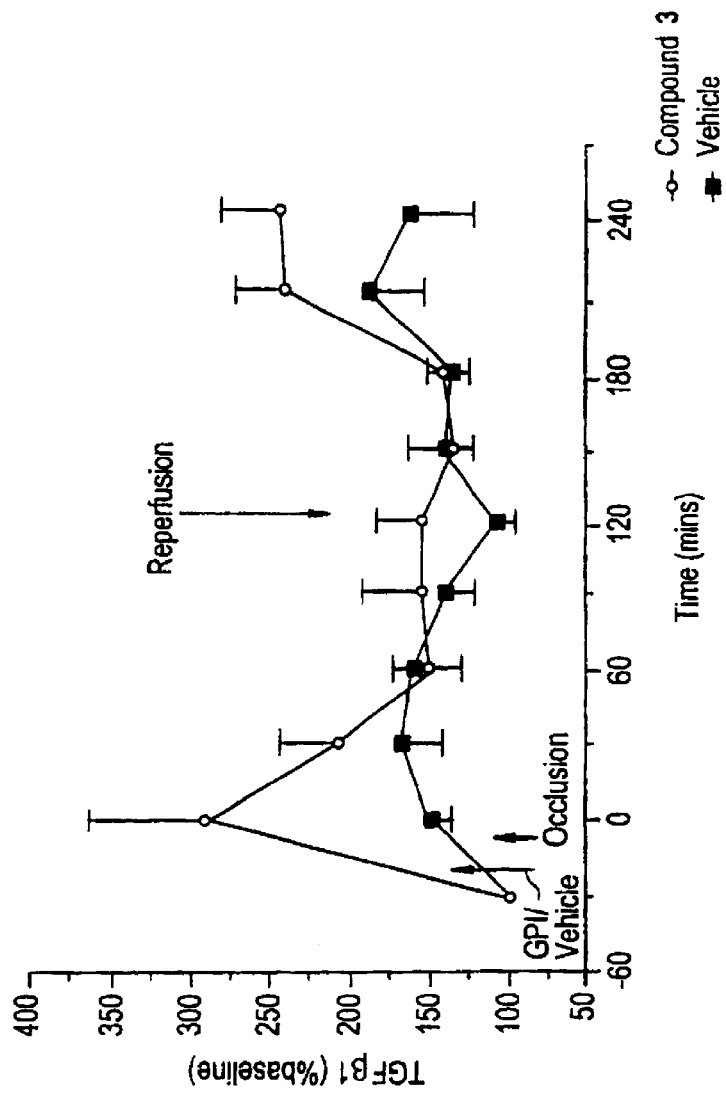

METHODS FOR TREATING CERTAIN DISEASES USING NAALADASE INHIBITORS

This application is a continuation of U.S. patent application Ser. No. 09/425,197, filed on Oct. 22, 1999, now U.S. Pat. No. 6,444,657, which is a continuation-in-part of U.S. patent application Ser. No. 09/224,291, filed on Dec. 31, 1998 now abandoned.

BACKGROUND OF THE INVENTION

The present invention relates to a method for regulating the release of transforming growth factor β (beta), commonly known as "TGF-β". More particularly, the invention relates to the use of TGF-β regulators to prevent and/or treat neural tissue damage resulting from ischemia and reperfusion injury, neurological disorders and other neurodegenerative diseases; to prevent or treat vascular stroke; or to treat or prevent other disorders such as arthritis, diabetes, inflammatory disorders, disorders of the immune system, and cancer.

Transforming growth factor β ("TGF-β") is recognized as a prototype of multifunctional growth factors. TGF-β regulates a variety of important cell and tissue functions, such as cell growth and differentiation, angiogenesis, immune function, extracellular matrix production, cell chemotaxis, apoptosis and hematopoiesis. Members of the TGF-β superfamily are widely distributed with most adult and embryonic tissues expressing at least one member of the family.

Active TGF-β is a disulfide-linked homodimer consisting of two chains of 112 amino acids. Following interchain disulfide bonding between two pro-TGF-β peptides, proteolytic processing at a tetrabasic site cleaves the mature TGF-β domain from the amino terminal portion of pro-TGF-β, which is called the latency associated protein (LAP). However, the mature TGF-β remains non-covalently associated with LAP, and this is the latent form of TGF-β that is secreted by most cells in vitro. The latent complex does not bind to the TGF-β receptor and so does not elicit a biological response. In vitro treatment of the latent complex with acid, alkali, chaotropic agents or heat releases biologically active TGF-β, but the in vivo mechanism of activation is not entirely clear. Since many cell types express both TGF-β and its receptor, however, the activation of latent TGF-β is thought to be a critical control point in regulating the diverse biological actions of TGF-β.

Biological actions of TGF-β are mediated through its binding to a heteromeric transmembrane receptor complex of two subunits designated type I (RI) and type II (RII), which are approximately 55 and 80 kDa, respectively. The current model of TGF-β ligand-receptor interaction proposes that RII, but not RI, can bind TGF-β. Binding of TGF-β to RII induces the assembly of a heterodimer of RII-RI, transphosphorylation of RI by RII, and then activation of signal transduction pathways to elicit a biological response. About six type II and four type I mammalian receptors have been cloned, and they demonstrate different specificities and affinities for binding to different members of the TGF-β superfamily.

It has recently been demonstrated that disruption of the TGF-β signaling pathway can be involved in the pathogenesis of human cancers. TGF-β is known to suppress the growth of epithelial cells, and a disruption of this pathway can lead to uncontrolled proliferation. Disruption at any point in the TGF-β signaling pathway can contribute to the loss of tumor suppressor activity. In the nervous system, it is thought that a loss of neuroprotective actions of TGF-β may result from mutations of components of the TGF-β signaling system in neurons and may contribute to chronic neurodegenerative disease.

One of the most well characterized in vivo actions of TGF-β is its ability to mediate a wound-healing cascade, which results in accelerated tissue repair. At the site of a peripheral wound, degranulation of platelets releases a bolus of TGF-β, which initiates a number of biological responses. Monocytes, lymphocytes, neutrophils and fibroblasts are recruited to the wound site as a result of chemotactic activity of TGF-β. Autoinduction of TGF-β in a number of cell types maintains high levels of the growth factor in the wound bend, where it induces angiogenesis and production of extracellular matrix to aid in tissue repair.

TGF-β may have similar functions with regard to tissue repair in the central nervous system as it does in peripheral organs. Neuronal injury can result from a variety of insults, including physical trauma, hypoxia, excitotoxins, cytotoxins, reactive oxygen species, neurotrophic factor deprivation or infection. The expression of TGF-β often increases in areas of neuronal dysfunction.

Additionally, TGF-β maintains neuronal survival and reduces infarct size in a number of animal or mammal models of stroke. A local inflammatory response occurs as part of the wound healing process of the central nervous system, and then resolves as the damaged area is repaired. The TGF-β produced by glial cells disappears as the inflammatory response subsides. In these circumstances, it appears that TGF-β may be effective in reducing neuronal damage or providing neuroprotection against damage, e.g., by the amyloid plaques of Alzheimer's diseases or excitatory insults.

The activation of metabotropic glutamate receptors (mGluR), which are selectively activated by N-acetylaspartylglutamate, in glial cultures has been reported to regulate the release of TGF-β. Bruno et al., "Neutralizing Antibodies for TGF-β2 Prevent Neuroprotection Mediated by Group-II Metabotropic Glutamate Receptors (mGluRs) in Cortical Cultures", *Neurosci. Abs.*, 2299 (1997); and Wroblewska et al., "N-Acetylaspartyglutamate Selectively Activates mGluR3 Receptors in Transfected Cells", *J. of Neurochemistry*, 69:1, 174–81 (1997). Thus, only a few naturally-occurring compounds have been used to increase TGF-β activity.

However, synthetic and purity issues often arise whenever naturally derived materials, proteins, or other large molecules, are used in vivo. Accordingly, there remains a need for relatively small molecules to regulate the release of endogenous TGF-β, both to produce more reliable effects and to simplify the synthesis of pharmaceutically useful compounds.

SUMMARY OF THE INVENTION

The present invention provides a method of treating a disease or condition in a mammal by administering an effective amount of a NAALADase inhibitor to said mammal in need of such treatment. The disease or condition may be selected from the group consisting of neurodegenerative disorders, cell-growth related diseases, infectious diseases, wound healing, immune related diseases, epithelial tissue scarring, collagen vascular diseases, fibroproliferative disorders, connective tissue disorders, inflammatory diseases, respiratory distress syndrome, and infertility.

In another embodiment, the disease or condition to be treated includes impaired immune function, extracellular matrix formation disorders, diabetes, autoimmune disorders, inflammatory diseases, cell-growth related disorders wherein the cells which are selected from the group consisting of kidney cells, hematopoietic cells, lymphocytes, epithelial cells, neuronal cells, and endothelial cells.

In yet another embodiment, the method includes treatment of a disease or condition that is evidenced by an abnormal level TGF-β.

BRIEF DESCRIPTION OF THE DRAWINGS

In the drawings, compound 3 is 2-(phosphonomethyl) pentanedioic acid.

FIG. 1 is a bar graph showing the effect on TGF-β1 concentration of compound 3 in cell cultures during a 20-minute ischemia.

FIG. 2 is a bar graph showing the effect on TGF-β2 concentration of compound 3 in cell cultures during a 20-minute ischemia.

FIG. 3 is a bar graph showing the reversal of the neuroprotective effect of compound 3 by TGF-β neutralizing antibodies.

FIG. 4 is a bar graph showing of the non-reversal of the neuroprotective effect of compound 3 by FGF neutralizing antibodies.

FIG. 5 is a bar graph showing the neuroprotective effect of compound 3 by following middle cerebral artery occlusion (MCAO) in rats pre-treated with TGF-β neutralizing antibodies.

FIG. 6 is a bar graph plotting TGF-β1 levels during ischemia and reperfusion following treatment of MCAO rats with compound 3, as compared to treatment with vehicle only.

DETAILED DESCRIPTION OF THE INVENTION

Definitions

"Compound 1" refers to pure and impure forms of 2-(2-sulfanylethyl) pentanedioic acid, or the compound prepared by Example 23.

"Compound 2" refers to 2-[[(2,3,4,5,6-pentafluorobenzyl) hydroxyphosphinyl]methyl]-pentanedioic acid.

"Compound 3" refers to 2-(phosphonomethyl)-pentanedioic acid (PMPA).

"Effective amount" refers to the amount required to produce the desired effect. "Therapeutically effective amount" refers to the amount required to treat diseases, disorders, or conditions recited herein or known by a person of skill in the art to be conducive to such treatment and in an amount capable of effecting, modifying, or detectably altering the treatment of the disease, disorder, or condition.

"Isosteres" refer to elements, molecules or ions having similar or identical physical properties due to similar or identical outer-shell electron arrangements. Two isosteric molecules must present similar or identical volumes and shapes. Ideally, isosteric compounds should be isomorphic and able to co-crystallize. Among the other physical properties that isosteric compounds usually share are boiling point, density, viscosity and thermal conductivity. However, certain properties must be different: dipolar moments, polarity, polarization, size and shape since the external orbitals may be hybridized differently. The Practice of Medicinal Chemistry, Academic Press, 1996.

"Carboxylic acid isosteres" include without limitation direct derivatives such as hydroxamic acids, acylcyanamides and acylsulfonamides; planar acidic heterocycles such as tetrazoles, mercaptoazoles, sulfinylazoles, sulfonylazoles, isoxazoles, isothiazoles, hydroxythiadiazole and hydroxychromes; and nonplanar sulfur- or phosphorus-derived acidic functions such as phosphinates, phosphonates, phosphonamides, sulphonates, sulphonamides, and acylsulphonamides. *The Practice of Medicinal Chemistry*, Academic Press, 1996.

"Metabolite" refers to a substance produced by metabolism or by a metabolic process.

"Pharmaceutically acceptable equivalent" includes without limitation pharmaceutically acceptable salts, hydrates, metabolites, prodrugs and carboxylic isosteres. Many pharmaceutically acceptable equivalents are expected to have-similar or the same in vitro or in vivo activity as the compounds of formulas I–VI.

"Pharmaceutically acceptable salt" refers to a salt of the inventive compounds which possesses the desired pharmacological activity and which is neither biologically nor otherwise undesirable. The salt can be formed with inorganic acids such as acetate, dipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts With amino acids such as arginine and lysine. Also, the basic nitrogen-containing groups can be quarternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995). For example, the inventive compounds can be transformed into prodrugs by converting one or more of the hydroxy or carboxy groups into esters.

"Alkyl" refers to a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" refers to a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, -pentenyl, n-hexenyl, and the like, unless otherwise indicated.

"Alkoxy" refers to the group —OR wherein R is alkyl as herein defined. Preferably, R is a branched or unbranched saturated hydrocarbon chain containing 1 to 6 carbon atoms.

"Aryl" means a carbocyclic or a heterocyclic aromatic moiety, which may be either unsubstituted or substituted. The term includes 5- to 8-membered mono-, bi- and tricyclic rings and fused rings, wherein the ring is either unsubstituted or substituted in one to five position(s) with halo, haloalkyl, hydroxyl, nitro, haloalkyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, thiocarbonyl, ester, thioester, cyano, imino, alkylamino, aminoalkyl, sulfhydryl, thioalkyl, and sulfonyl. When the aryl ring is heterocyclic, it may contain from 1–4 heteroatom (s) selected from the group consisting of O, N, and S. The term "aryl" includes the case where an aromatic or tertiary alkyl amines are oxidized to a corresponding N-oxide.

"Phenyl" includes all possible isomeric phenyl radicals, optionally monosubstituted or multi-substituted with non-interfering substituents selected from the group consisting of amino, imino, alkylamino, aminoalkyl, —$NR_2$ wherein $R_2$ is selected from the group consisting of hydrogen, ($C_1$–$C_6$)-straight or branched chain alkyl, ($C_3$–$C_6$)-straight or branched chain alkenyl or alkynyl; halo; haloalkyl such as trifluoromethyl and iodo-isopropyl; hydroxy; $C_1$–$C_6$ straight- or branched-chain alkyl; $C_2$–$C_6$ straight- or branched-chain alkenyl; carbonyl or thiocarbonyl; ester or thioester; alkoxy or alkenoxy; cyano; nitro; sulfhydryl, thioalkyl, or sulfonyl: and ($C_1$–$C_4$) bridging alkyl, such as when a bridging alkyl substituent forms a fused heterocyclic ring with the aryl group.

"Halo" or "halogen" refers to fluoro, chloro, bromo and iodo, unless otherwise indicated.

"Isomers" refer to compounds having the same number and kind of atoms, and hence the same molecular weight, but differing in respect to the arrangement or configuration of the atoms.

"Stereoisomers" refer to compounds which have identical chemical constitution, but differ as regards to the arrangement of the atoms or groups in space.

"Optical isomers" refer to either of two-kinds of stereoisomers. One kind is represented by mirror-image structures called enantiomers, which result from the presence of one or more asymmetric carbon atoms in the compound (glyceraldehyde, lactic acid, sugars, tartaric acid, amino acids). The other kind is exemplified by diastereoisomers, which are not mirror images. These occur in compounds having two or more asymmetric carbon atoms; thus, such compounds have $2_n$ optical isomers, where n is the number of asymmetric carbon atoms.

"Enantiomers" refer to stereoisomers which are non-superimposable mirror images of one another.

"Enantiomer-enriched" refers to a mixture in which one enantiomer predominates.

"Racemic" refers to a mixture containing equal parts of individual enantiomers.

"Non-racemic" refers to a mixture containing unequal parts of individual enantiomers.

"Animal or mammal" refers to a living organism having sensation and the power of voluntary movement and requires oxygen and organic food for its existence. Examples include without limitation a mammal such as a member of the human, equine, porcine, bovine, murine, canine or feline species. In the case of a human, the term "animal or mammal" may also be referred to as a "patient".

"Disease" refers to any deviation from or interruption of the normal structure or function of any part, organ, or system (or combination thereof) of the body that is manifested by a characteristic set of symptoms and signs and whose etiology, pathology, and prognosis may be known or unknown. *Dorland's Illustrated Medical Dictionary*, W. B. Saunders Co., 27th ed. (1988).

"Disorder" refers to any derangement or abnormality of function; a morbid physical or mental state. *Dorland's Illustrated Medical Dictionary*, W. B. Saunders Co., 27th ed. (1988).

The term "release", as used herein covers the giving up of TGF-β into a substance.

The term "TGF-β" as used herein refers to transforming growth factor beta.

The term "regulation", in the context of endogenous release, relates to the production of a statistically significant increase in the exogenous concentration of TGF-β as compared with the concentration occurring in the absence of the compound of the invention. Preferably, this is a physiologically significant amount resulting in the observation of a desired biological effect either in vitro or in vivo.

The term "treatment" as used herein covers any treatment of a disease and/or condition in an animal or mammal, particularly a human, and includes:

(i) preventing a disease, disorder and/or condition from occurring in a person which may be predisposed to the disease, disorder and/or condition but has not yet been diagnosed as having it;

(ii) inhibiting the disease, disorder and/or condition, i.e., arresting its development; and (iii) relieving the disease, disorder and/or condition, i.e., causing regression of the disease, disorder and/or condition.

"Acid containing metal chelator" refers to any compound having (i) a functional group capable of interacting with the metal(s) at the active site of the NAALADase enzyme; and (ii) an acid portion which interacts at the recognition site of the NAALADase enzyme.

"NAALADase related disease or disorder" refers to any disease or disorder specifically known in the art to be capable of treatment by administration of a NAALADase inhibitor.

"Neuroregenerative disorder" refers to conditions and disorders where neurons have been damaged surgically, is chemically, by acute or chronic disease process such as diabetes, Alzheimer's, or Parkinson's, Guillain Barre, or similar events and wherein the neurons are actively stimulated or promoted to regrow or regenerate in a manner similar to the neurotrophic actions of nerve growth factors but distinct from passive treatments known in the art such as the prevention of further neurodegeneration and neuroprotective effects.

"Abnormal level of TGF-β" refers to a measurable variance from normal levels of TGF-β as determined by persons of ordinary skill in the art and which is the causative agent of, associated with, mediates through, or evidences TGF-β related conditions, diseases, disorders, or pathologies.

Naaladase Inhibitors

Although not limited to any one particular theory, it is believed that the NAALADase inhibitors used in the inventive methods and pharmaceutical compositions modulate levels of TGF-β and in particular by increasing TGF-β levels, and/or the NAALADase inhibitors are believed to inhibit myeloperoxidase activity.

A preferred NAALADase inhibitor is a compound of formula I:

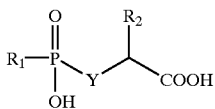

or a pharmaceutically acceptable equivalent, wherein:

Y is $CR_3R_4$, $NR_5$ or O;

$R_1$ is selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl, Ar, COOR, $NR_6R_7$ and OR, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, COOR, $NR_6R_7$ and Ar;

$R_2$ is selected from the group consisting of hydrogen, $C_1$–$C_6$ alkyl, $C_2$–$C_6$ alkenyl, $C_3$–$C_8$ cycloalkyl, $C_5$–$C_7$ cycloalkenyl, Ar, halo and carboxy, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, $NR_6R_7$ and Ar;

$R_3$ and $R_4$ are independently hydrogen or $C_1$–$C_3$ alkyl;

$R_5$ is hydrogen or $C_1$–$C_3$ alkyl;

R, $R_6$ and $R_7$ are independently selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl and Ar, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl and phenyl, wherein said Ar is unsubstituted or substituted with one or more substituent(s) independently selected from the group consisting of halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, carboxy and $NR_1R_2$.

Preferably, Y is $CH_2$.

More preferably, when Y is $CH_2$, then $R_2$ is —$(CH_2)_2COOH$.

Most preferably, when Y is $CH_2$ and $R_2$ is —$(CH_2)_2COOH$, then $R_1$ is hydrogen, $C_1$–$C_4$ alkyl, $C_2$–$C_4$ alkenyl, $C_3$–$C_8$ cycloalkyl, $C_5$–$C_7$ cycloalkenyl, benzyl, phenyl or OR, wherein said alkyl, alkenyl, cycloalkyl, cycloalkenyl, benzyl and phenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, $NR_6R_7$, benzyl and phenyl.

Preferred compounds of formula I are selected from the group consisting of:

2-(phosphonomethyl)pentanedioic acid;
2-[[(2-carboxyethyl)hydroxyphosphinyl]methyl]-pentanedioic acid;
2-[(benzylhydroxyphosphinyl)methyl]pentanedioic acid;
2-[(phenylhydroxyphosphinyl)methyl]pentanedioic acid;
2-[[((hydroxy)phenylmethyl)hydroxyphosphinyl]-methyl]pentanedioic acid;
2-[(butylhydroxyphosphinyl)methyl]pentanedioic acid;
2-[[(3-methylbenzyl)hydroxyphosphinyl]methyl]-pentanedioic acid;
2-[(3-phenylpropylhydroxyphosphinyl)methyl]-pentanedioic acid;
2-[[(4-fluorophenyl)hydroxyphosphinyl]methyl]-pentanedioic acid;
2-[(methylhydroxyphosphinyl)methyl]pentanedioic acid;
2-[(phenylethylhydroxyphosphinyl)methyl]-pentanedioic acid;
2-[[(4-methylbenzyl)hydroxyphosphinyl]methyl]-pentanedioic acid;
2-[[(4-fluorobenzyl)hydroxyphosphinyl]methyl]-pentanedioic acid;
2-[[(4-methoxybenzyl)hydroxyphosphinyl]methyl]-pentanedioic acid;
2-[[(3-trifluoromethylbenzyl)hydroxyphosphinyl]-methyl]pentanedioic acid;
2-[[4-trifluoromethylbenzyl)hydroxyphosphinyl]-methyl]pentanedioic acid;
2-[[(2-fluorobenzyl)hydroxyphosphinyl]methyl]-pentanedioic acid;
2-[[(2,3,4,5,6-pentafluorobenzyl)hydroxy-phosphinyl]methyl]pentanedioic acid; and
pharmaceutically acceptable equivalents.

More preferably, the compound of formula I is 2-[[(2,3,4,5,6-pentafluorobenzyl)hydroxyphosphinyl]-methyl]pentanedioic acid or a pharmaceutically acceptable equivalent. Most preferably, the compound of formula I is an enantiomer or an enantiomer-enriched mixture.

Representative compounds of formula I wherein $R_1$ is substituted with COOR include without limitation:

2-[[2-carboxypropyl)hydroxyphosphinyl]methyl]-pentanedioic acid;
2-[[2-carboxybutyl)hydroxyphosphinyl]methyl]-pentanedioic acid;
2-[[(2-carboxypentyl)hydroxyphosphinyl]methyl]-pentanedioic acid;
2-[[(2-carboxy-3-phenylpropyl)hydroxyphosphinyl]-methyl]pentanedioic acid;
2-[[2-carboxy-3-naphthylpropyl)hydroxy-phosphinyl]methyl]pentanedioic acid;
2-[[2-carboxy-3-pyridylpropyl)hydroxyphosphinyl]-methyl]pentanedioic acid;
2-[[2-benzyloxycarbonyl)-3-phenylpropyl)hydroxy-phosphinyl]methyl]pentanedioic acid;
2-[[2-methoxycarbonyl)-3-phenylpropyl)hydroxy-phosphinyl]methyl]pentanedioic acid;
2-[[(3-carboxy-2-methoxycarbonyl)propyl)hydroxy-phosphinyl]methyl]pentanedioic acid;
2-[[(4-carboxy-2-methoxycarbonyl)butyl)hydroxy-phosphinyl]methyl]pentanedioic acid; and
pharmaceutically acceptable equivalents.

Representative compounds of formula I wherein $R_1$ is substituted with $NR_6R_7$ include without limitation:

2-[({[Benzylamino]benzyl}(hydroxyphosphinyl))-methyl]pentanedioic acid;
2-[({[Carboxyamino]benzyl}(hydroxyphosphinyl))-methyl]pentanedioic acid;
2-[({[Benzylamino]methyl}(hydroxyphosphinyl))-methyl]pentanedioic acid;
2-[({[Acetylamino]methyl}(hydroxyphosphinyl))-methyl]pentanedioic acid;
2-[({[Diphenylamino]methyl}(hydroxyphosphinyl))-methyl]pentanedioic acid;
2-[({[Phenylamino]methyl}(hydroxyphosphinyl))-methyl]pentanedioic acid;
2-({[(Phenylcarboxamido)methyl](hydroxy-phosphinyl)}methyl)pentanedioic acid;
2-({[(Phenylsulfonamido)methyl](hydroxy-phosphinyl)}methyl)pentanedioic acid;
2-[({[(4-Fluorophenyl)amino]methyl}(hydroxy-phosphinyl))methyl]pentanedioic acid;
2-[({[(4-Methoxyphenyl)amino]methyl}(hydroxy-phosphinyl))methyl]pentanedioic acid;
2-[({[(4-Methylphenyl)amino]methyl}-(hydroxyphosphinyl))methyl]pentanedioic acid;
2-[({[(4-Tert-butylphenyl)amino]methyl}-(hydroxyphosphinyl))methyl]pentanedioic acid;
2-[({[(Thioformanilido)amino]benzyl}-(hydroxyphosphinyl))methyl]pentanedioic acid;
2-[({[1,3-Dioxo-2,3-dihydro-1H-2-isoindolyl]methyl}hydroxyphosphinyl)methyl]-pentanedioic acid; and
pharmaceutically acceptable equivalents.

Another preferred NAALADase inhibitor is a compound of formula II:

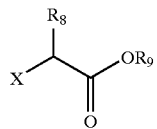

II or a pharmaceutically acceptable equivalent, wherein:
X is a moiety of formula (III), (IV) or (V):

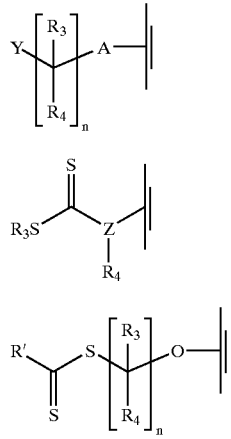

m and n are independently 0, 1, 2, 3 or 4;
Z is $SR_{13}$, $SO_3R_{13}$, $SO_2R_{13}$, $SOR_{13}$, $SO(NR_{13})R_{14}$ or $S(N_2R_{13}R_{14})R_{15}$;
B is N or $CR_{16}$;
A is O, S, $CR_{17}R_{18}$ or $(CR_{17}R_{18})_mS$;
$R_8$, $R_9$, $R_{10}$, $R_{11}$, $R_{12}$, $R_{13}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and
$Ar_1$ is a carbocyclic or heterocyclic moiety, which is unsubstituted or substituted with one or more substituent(s); provided that when X is a moiety of formula III and A is O, then n is 2, 3 or 4; when X is a moiety of formula III and A is S, then n is 2, 3 or 4; and when X is a moiety of formula III and A is $(CR_{17}R_{18})_mS$, then n is 0, 2, 3 or 4.

Possible substituents of said alkenyl, cycloalkyl, cycloalkenyl, and Ar, include without limitation $C_1$–$C_9$ alkyl, $C_2$–$C_9$ chain alkenyl, $C_1$–$C_9$ alkoxy, $C_2$–$C_9$ alkenyloxy, phenoxy, benzyloxy, $C_3$–$C_3$ cycloalkyl, $C_5$–$C_7$ cycloalkenyl, hydroxy, carboxy, carbonyl, amino, amido, cyano, isocyano, nitro, nitroso, nitrilo, isonitrilo, imino, azo, diazo, sulfonyl, sulfoxy, thio, thiocarbonyl, thiocyano, formanilido, thioformamido, sulfhydryl, halo, haloalkyl, trifluoromethyl, and carbocyclic and heterocyclic moieties. Carbocyclic moieties include alicyclic and aromatic structures.

Examples of useful carbocyclic and heterocyclic moieties include without limitation phenyl, benzyl, naphthyl, indenyl, azulenyl, fluorenyl, anthracenyl, indolyl, isoindolyl, indolinyl, benzofuranyl, benzothiophenyl, indazolyl, benzimidazolyl, benzthiazolyl, tetrahydrofuranyl, tetrahydropyranyl, pyridyl, pyrrolyl, pyrrolidinyl, pyridinyl, pyrimidinyl, purinyl, quinolinyl, isoquinolinyl, tetrahydroquinolinyl, quinolizinyl, furyl, thiophenyl, imidazolyl, oxazolyl, benzoxazolyl, thiazolyl, isoxazolyl, isotriazolyl, oxadiazolyl, triazolyl, thiadiazolyl, pyridazinyl, pyrimidinyl, pyrazinyl, triazinyl, trithianyl, indolizinyl, pyrazolyl, pyrazolinyl, pyrazolidinyl, thienyl, tetrahydroisoquinolinyl, cinnolinyl, phthalazinyl, quinazolinyl, quinoxalinyl, naphthyridinyl, pteridinyl, carbazolyl, acridinyl, phenazinyl, phenothiazinyl, and phenoxazinyl.

Representative compounds of formula II wherein X is a moiety of formula IV, $R_8$ is —$(CH_2)_2COOH$, $R_9$ is hydrogen, and B is $CR_{16}$, include without limitation:

2-(dithiocarboxymethyl)pentanedioic acid;
2-(1-dithiocarboxyethyl)pentanedioic acid; and
pharmaceutically acceptable equivalents.

Representative compounds of formula II wherein X is a moiety of formula IV, $R_9$ is —$(CH_2)_2COOH$, $R_9$ is hydrogen, and B is N, include without limitation:

2-dithiocarboxyaminopentanedioic acid;
2-[(N-methyldithiocarboxy)amino]pentanedioic acid; and
pharmaceutically acceptable equivalents.

Representative compounds of formula II wherein X is a moiety of formula V include without limitation:

2-benzyl-4-sulfanylbutanoic acid;
2-benzyl-4-sulfanylpentanoic acid;

2-(3-pyridylmethyl)-4-sulfanylpentanoic acid;
2-(3-pyridylmethyl)-4-sulfanylhexanoic acid;
2-benzyl-3-sulfanylpropanoic acid;
2-benzyl-3-sulfanylpentanoic acid;
2-(4-pyridylmethyl)-3-sulfanylpentanoic acid; and
pharmaceutically acceptable equivalents.

In a preferred embodiment of formula II, the NAALA-Dase inhibitor is a compound of formula VI:

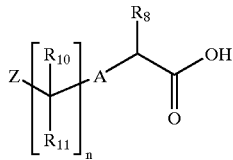

VI or a pharmaceutically acceptable equivalent, wherein:
n is 0, 1, 2 or 3;
Z is SH, $SO_3R_{13}$, $SO_2R_{13}$, $SOR_{13}$ or $S(N_2R_{13}R_{14})R_{15}$; and
A is $CR_{17}R_{18}$.
Preferably, Z is SH.
More preferably, when Z is SH, then $R_8$ is —$(CH_2)_2COOH$.
Preferred compounds of formula VI are selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

More preferably, the compound of formula VI is selected from the group consisting of 2-(2-sulfanylethyl) pentanedioic acid, 2-(2-sulfanylpropyl)-pentanedioic acid, 2-(3-sulfanylpropyl)pentanedioic acid and pharmaceutically acceptable equivalents. Most preferably, the compound of formula VI is an enantiomer or an enantiomer-enriched mixture.

Other NAALADase inhibitors are described in U.S. Pat. Nos. 5,672,592, 5,795,877, 5,863,536, 5,880,112, 5,962, 251, 5,968,915, 5,902,817 and 6,054,444, the entire contents of which patents are herein incorporated by reference.

The compounds used in the methods and pharmaceutical compositions of the present invention possess one or more asymmetric carbon center(s) and are thus capable of existing in the form of optical isomers as well as in the form of racemic or non-racemic mixtures of optical isomers. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules, for example, esters, amides, acetals, ketals, and the like, by reacting compounds used in the inventive methods and pharmaceutical compositions with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the parent optically active drug is not necessary prior to dosing the patient since the compound can behave as a prodrug. The optically active compounds used in the inventive methods and pharmaceutical compositions can likewise be obtained by utilizing optically active starting materials.

It is understood that the compounds used in the inventive methods and pharmaceutical compositions encompass optical isomers as well as racemic and non-racemic mixtures.

Synthesis of NAALADase Inhibitors

The NAALADase inhibitors of formula I can be readily prepared by standard techniques of organic chemistry. Precursor compounds can be prepared by methods known in the art, such as those described by Jackson et al., *J. Med. Chem.*, Vol. 39, No. 2, pp. 619–622 (1996) and Froestl et al., *J. Med. Chem.*, Vol. 38, pp. 3313–3331 (1995).

Various means of synthesizing NAALADase inhibitors can be found in *J. Med. Chem.*, Vol. 31, pp. 204–212 (1988); *J. Med. Chem.*, Vol. 39, pp. 619–622 (1996); WO 98/45,256, published Oct. 15, 1998; WO 98/45,257, published Oct. 15, 1998; and WO 98/13044, published Apr. 2, 1998, incorporated herein by reference in their entirety.

Some of the NAALADase inhibitors used in the inventive methods and pharmaceutical compositions can be readily prepared by standard techniques of organic chemistry, utilizing the general synthetic pathways depicted in U.S. Pat. Nos. 5,672,592, 5,795,877, 5,863,536, 5,880,112, 5,962, 521, 5,968,915, 5,902,817, and 6,054,444, the entire contents of which patents are herein incorporated by reference.

Methods of the Present Invention

Cell Growth

The present invention provides methods for stimulating growth of tissue, glands, or organs in an animal or mammal, the method comprising administering an effective amount of a NAALADase inhibitor to said animal or mammal. In a preferred embodiment, the growth of tissue, glands, or organs enhances milk production or weight gain in an animal or mammal.

In another embodiment, the present invention provides methods for treating cell-growth related disorders in an animal or mammal, the method comprising administering an effective amount of a NAALADase inhibitor to said animal or mammal. In a preferred aspect of this embodiment, the treated cells are selected from the group consisting of kidney cells, hematopoietic cells, lymphocytes, epithelial cells, and endothelial cells.

In yet another embodiment, the present invention provides methods for treating neurodegenerative disorders in an animal or mammal, the method comprising administering an effective amount of a NAALADase inhibitor to said animal or mammal. In a preferred aspect of this embodiment, the neurodegenerative disorder is selected from the group consisting of neural tissue damage resulting from ischemia reperfusion injury, myelination, and neuroregeneration.

In yet another embodiment, the present invention provides methods for treating a disease state in an animal or mammal, the method comprising administering an effective amount of a NAALADase inhibitor to said animal or mammal.

In a preferred aspect of this embodiment, the disease state is selected from the group consisting of stimulation of cell proliferation, cell growth inhibition, regulation of extracellular matrix proteins, atherosclerosis, autocrine tumors, fibroplasia, and keloid formation.

In yet another preferred aspect, the stimulation of cell proliferation is selected from the group consisting of induced proliferation of fibroblasts in semi-solid medium, growth or mesenchymal cells, and stimulation of chrondrogenesis, osteogenesis, and epithelial cell differentiation.

In yet another preferred aspect, the cell growth inhibition is selected from the group consisting of inhibition of the proliferation of epithelial cells, endothelial cells, T and B lymphocytes, and thymoctes, inhibition of expression of adipose, skeletal muscle, and hematopoietic phenotypes, neoplasms, non-cytocidal viral or other pathogenic infections, and autoimmune disorders.

An especially preferred aspect is where the non-cytocidal viral or other pathogenic infection is selected from the group consisting of AIDS, herpes, CMV (cytomegalovirus), EBV (Epstein Barr Virus), and SSPE (subacute sclerosis panencephalitis).

Another preferred aspect is where the disease state is selected from the group consisting of pathogenesis glomerulonepritis, liver cirrhosis, and pulmonary fibrosis.

Infectious Disease

In still another embodiment, the present invention provides methods for treating a mammal afflicted with an infectious disease caused by a macrophage pathogen, the method comprising administering an effective amount of a NAALADase inhibitor to said mammal.

A preferred aspect of this embodiment is where a macrophage pathogen is selected from the group consisting of bacteria, yeast, fungi, viruses, protozoa, *Trypanosoma cruzi, Histoplasma capsulatum, Candida albicans, Candida parapsilosis, Cryptococcus neoformans, Salmonella, Pneumocystis*, Toxoplasma, Listeria, Mycobacteria, Rickettsia, Leishmania, and combinations thereof.

Especially preferred Mycobacteria include *Mycobacterium tuberculosis* and *Mycobacterium leprae*. Especially preferred Toxoplasma include *Toxoplasma gondii*. Especially preferred Rickettsia include *R. prowazekii, R. coronii*, and *R. tsutsugamushi*.

Preferred infectious diseases treated by this method include single or multiple cutaneous lesions, mucosal disease, Chagas' disease, acquired immunodeficiency syndrome (AIDS), toxoplasmosis, leishmaniasis, trypanosomiasis, shistosomiasis, cryptosporidiosis, *Mycobacterium avium* infections, *Pneumocystis carinii* pneumonia, and leprosy.

Mediating Disease Resistance and Susceptibility

In another embodiment, the present invention provides methods for mediating disease resistance and susceptibility in an animal or mammal, the method comprising administering an effective amount of a NAALADase inhibitor to said animal or mammal.

Immunosuppression

In yet another embodiment, the present invention provides methods for suppressing the cellular immune response in an animal or mammal, the method comprising administering an effective amount of a NAALADase inhibitor to said animal or mammal.

In still another embodiment, the present invention provides methods for providing a therapeutic treatment in an animal or mammal, the method comprising administering an effective amount of a NAALADase inhibitor to said animal or mammal.

In still another embodiment, the present invention provides methods for treating immunosuppression associated with an infectious disease in an animal or mammal, the method comprising administering an effective amount of a NAALADase inhibitor to said animal or mammal.

Preferably, the immunosuppression is associated with trypanosomal infection, viral infection, human immunosuppression virus, human T cell lymphotropic virus (HTLV-1), lymphocytic choriomeningitis virus, and hepatitis.

Various TGF-$\beta$ Related Disorders

Preferred therapeutic treatments include inhibiting germ cell division, inhibiting arotamase in developing ovaries, preventing or alleviating Respiratory Distress Syndrome in newborns, treating infertility, blocking tyrosine autophosphorylation of EGF receptors, and repairing retarded bone growth or traumatic bone injury.

In another embodiment, the present invention provides methods for mitigation of radiation induced tissue damage in an animal or mammal, the method comprising administering an effective amount of a NAALADase inhibitor to said animal or mammal.

Preferred tissue damages to be treated include fibrosis, remodeling of the extracellular matrix, vascular damage, aberrant angiogenesis, pneuminitis, atherogenesis, osteonecrosis, mucositis, immunosuppression, and functional impairment. Preferred tissues to be treated by this method include liver, lung, gastrointestinal tract, kidneys, breast, testes, salivary gland, mucosa, skin, and brain. Breast tissue is especially preferred.

Wound Treatment

In yet another embodiment, the present invention provides methods for inhibiting scar tissue formation during the treatment of wounds, the method comprising administering an effective amount of a NAALADase inhibitor to a host suffering from tissue wounding.

Preferred tissues to be treated by this method include skin or other epithelial tissue. Preferably, the tissue has been damaged by wounds resulting from accidental injury, surgical operations, trauma-induced lacerations, wounds involving the peritoneum for which the excessive connective tissue formation is abdominal adhesions, or other trauma. In an especially preferred embodiment, the NAALADase inhibitor is administered at an early stage of healing.

Collagen Vascular Diseases

In still another embodiment, the present invention provides methods for treating a collagen vascular disease in an animal or mammal, the method comprising administering an effective amount of a NAALADase inhibitor to said animal or mammal.

Preferred collagen vascular diseases to be treated include progressive systemic sclerosis (PSS), polymyositis, scleroderma, dermatomyositis, eosinophilic fascitis, morphea, Raynaud's syndrome, interstitial pulmonary fibrosis, scleroderma, or systemic lupus erythematosus.

Fibroproliferative Disorders

In another embodiment, the present invention provides methods for treating a fibroproliferative disorder in an animal or mammal, the method comprising administering an effective amount of a NAALADase inhibitor to said animal or mammal.

Preferred fibroproliferative disorders to be treated include diabetic nephropathy, kidney disease, proliferative vitreoretinopathy, liver cirrhosis, biliary fibrosis, and myelofibrosis. Especially preferred kidney diseases include mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Connective Tissue Disorders

In yet another embodiment, the present invention provides methods for treating a connective tissue disorder in an animal or mammal, the method comprising administering an effective amount of a NAALADase inhibitor to said animal or mammal.

Preferred connective tissue disorders to be treated include scleroderma, myelofibrosis, and hepatic, intraocular, and pulmonary fibrosis.

Immune Mediation

In another embodiment, the present invention provides methods for increasing the effectiveness of a vaccine, the method comprising administering an effective amount of a NAALADase inhibitor to an individual about to receive a vaccine or receiving a vaccine.

In yet another embodiment, the present invention provides methods for treating an allergy in an animal or mammal, the method comprising administering an effective amount of a NAALADase inhibitor to said animal or mammal.

Preferably, the allergy is selected from the group consisting of allergy to dust and hay fever.

Polyp Formation

In still another embodiment, the present invention provides methods for inhibiting polyp formation in an animal or mammal, the method comprising administering an effective amount of a NAALADase inhibitor to said animal or mammal.

Preferably, the polyp can be formed in the nose or the intestine.

Inflammatory Diseases

In yet another embodiment, the present invention provides methods for treating inflammatory diseases. Without being limited to a particular mechanism, it appears that the compounds of the present invention operate through two potential modes of action. The first, mediation and regulation of TGF-β, provides an effective treatment of inflammatory diseases. The second, inhibition of myeloperoxidase, is also thought to provide an effective way to ameliorate inflammatory diseases.

Preferably, the inflammatory disease is associated with: progressive systemic sclerosis (PSS), polymyositis, scleroderma, dermatomyositis, eosinophilic fasciitis, morphea, Raynaud's syndrome, interstitial pulmonary fibrosis, scleroderma, systemic lupus erythematosus, diabetic nephropathy, kidney disease, proliferative vitreoretinopathy, liver cirrhosis, biliary fibrosis, and myelofibrosis, mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Route of Administration

In the methods of the present invention, the NAALADase inhibitors may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the NAALADase inhibitors should readily penetrate the blood-brain barrier when peripherally administered. Compounds which cannot penetrate the blood-brain barrier can be effectively administered by an intraventricular route.

The NAALADase inhibitors may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the NAALADase inhibitors may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The NAALADase inhibitors may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the NAALADase inhibitors may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The NAALADase inhibitors used in the methods of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

Dosage

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal or mammal models are also helpful. The considerations for determining the proper dose levels are well known in she art.

In a preferred embodiment, the NAALADase inhibitors are administered in lyophilized form. In this case, 1 to 100 mg of a NAALADase inhibitor may be lyophilized in individual vials, together with a carrier and a buffer, such as mannitol and sodium phosphate. The compound may be reconstituted in the vials with bacteriostatic water before administration.

The NAALADase inhibitors used in the inventive methods may be administered in combination with one or more therapeutic agents. Specific dose levels for these agents will depend upon considerations such as those identified above.

Administration Regimen

For the methods of the present invention, any administration regimen regulating the timing and sequence of drug delivery can be used and repeated as necessary to effect treatment. Such regimen may include pretreatment and/or co-administration with additional therapeutic agents.

Combination With Other Treatments

In the inventive methods, the NAALADase inhibitors can be co-administered with one or more additional therapeutic agent(s), preferably other anxiolytic agents, memory enhancing agents or agents capable of treating the underlying cause of memory impairment.

Examples of anxiolytic agents which may be combined with the NAALADase inhibitors include without limitation benzodiazepines (chlordiazepoxide, diazepam, clorazepate, flurazepam, halazepam, prazepam, clonazepam, quazepam, alprazolam, lorazepam, oxazepam, temazepam, triazolam); barbiturates; $\beta$ blockers; and buspirone.

The NAALADase inhibitors can be co-administered with one or more therapeutic agents either (i) together in a single formulation, or (ii) separately in individual formulations designed for optimal release rates of their respective active agent. Each formulation may contain from about 0.01% to about 99.99% by weight, preferably from about 3.5% to about 60% by weight, of a NAALADase inhibitor, as well as one or more pharmaceutical excipients, such as wetting, emulsifying and pH buffering agents.

The present neurotrophic NAALADase inhibitors can be administered with other therapeutic agents.

The following examples are illustrative of the present invention and are not intended to be limitations thereon. Unless otherwise indicated, all percentages are based upon 100% by weight of the final composition.

EXAMPLES

Example 1

Cell Culture Data

The compounds of the invention were used to produce a neuroprotective effect in both in vitro and in vivo cell culture models of stroke. Specifically, when 2-(phosphonomethyl)-pentanedioic acid was added to ischemic cultures, the level of TGF-$\beta$1 and TGF-$\beta$2 increased significantly (see FIGS. 1 and 2). This data shows that the compounds of the present invention promote the release of significantly increased amounts of endogenous TGF-$\beta$s from glial cells, and this, in turn, provides neuroprotection for neighboring neurons.

TGF-$\beta$ neutralizing antibodies were then added to determine if the neuroprotective effect would be blocked. The neuroprotective effect of 2-(phosphonomethyl)pentanedioic acid was blocked by TGF-$\beta$s neutralizing bodies in this cell culture model (see FIG. 3). However, when other growth factor antibodies, such as FGF antibody, were added, the neuroprotective effect of 2-(phosphonomethyl)pentanedioic acid was not reversed in culture (see FIG. 4). This indicates that the compounds are directly related to the TGF-$\beta$ levels, during stroke.

Example 2

In Vivo Stroke Model Data

The effect of TGF-$\beta$ neutralizing antibodies on the neuroprotection afforded by 2-(phosphonomethyl)-pentanedioic acid following middle cerebral artery occlusion (MCAO) in rats was also studied to give a more relevant in vivo model of stroke. Treatment of MCAO rats with 2-(phosphonomethyl)pentanedioic acid caused a significant rise in TGF-$\beta$1 during both occlusion and reperfusion, as assessed by microdialysis, as shown in FIG. 6. This data showed that the compounds of the invention, exemplified by 2-(phosphonomethyl) pentanedioic acid, provided neuroprotection, at least in part by regulating endogenous transforming growth factors.

Additionally, antibodies which neutralize TGF-$\beta$, significantly attenuated the neuroprotective effect of 2-(phosphonomethyl) pentanedioic acid, in vivo, as shown in FIG. 5. Thus, it was appreciated that the regulation of TGF-$\beta$s may have implications, not only in its utility in stroke, but also in other neurological and psychiatric diseases. In addition, this mechanism may have implications in myelination, prostate cancer, inflammation, diabetes, and angiogenesis.

Example 3

In Vivo Toxicity Studies

The in vivo toxicological effect of NAALADase inhibition has been examined in mice. The results show that NAALADase inhibitors are non-toxic to mice, suggesting that it would be similarly non-toxic to humans when administered at therapeutically effective amounts. Representative disclosure may be found in U.S. Pat. Nos. 5,672,592, 5,795,877, 5,863,536, 5,880,112, 5,962,251, 5,968,915, 5,902,817 and 6,054,444, the entire contents of which patents are herein incorporated by reference.

To examine the toxicological effect of the compounds of the invention in vivo, a group of mice were injected with 2-(phosphonomethyl)pentanedioic acid in doses of 1, 5, 10, 30, 100, 300 and 500 mg/kg body weight. The mice were observed two times per day for 5 consecutive days. The survival rate at each dose level is provided below in TABLE I. The results showed that the compound of the invention was non-toxic to mice, suggesting that it would be similarly non-toxic to humans when administered at therapeutically effective amounts.

TABLE I

TOXICOLOGICAL EFFECTS OF PROMOTER COMPOUNDS

| | Dose (mg/kg) | | | | | | |
|---|---|---|---|---|---|---|---|
| | 1 | 5 | 10 | 30 | 100 | 300 | 500 |
| Survival Rate After 5 days (%) | 100 | 100 | 100 | 100 | 100 | 100 | 66.7 |

Example 4

In Vitro Inhibition of NAALADase Activity

Various compounds used in the inventive methods and pharmaceutical compositions have been tested for in vitro inhibition of NAALADase activity. Some of the results are set forth in U.S. Pat. Nos. 5,672,592, 5,795,877, 5,863,536, 5,880,112, 5,962,251, 5,968,915, 5,902,817 and 6,054,444, the entire contents of which patents are herein incorporated by reference.

Example 5

Myeloperoxidase (human)/Inflammation

Myeloperoxidase (MPO, EC 1.11.1.7) is a main constituent of azurophilic granules in neutrophils. Its function(s) is (are) still uncertain, but when combined with a halide and $H_2O_2$ it forms a highly toxic system, which can kill microorganisms, injure host cells and inactivate humoral factors (reviewed by Klebanoff & Clark, 1978; Clark, 1983).

MPO was first isolated by Agner (1941), and subsequently the enzyme was purified in crystalline form (Agner, 1958; Harrison et al., 1977). Felberg & Schultz (1972) demonstrated, by polyacrylamide-gel electrophoresis, the herterogeneity of MPO isolated from leucocytes from pooled blood of several donors. Later, Strauven et al. (1978) obtained four isoenzymes from single donors, and the relative amounts seemed to vary with the age of the donors. More recently, three forms were isolated from HL-60 cells (Yamada et al., 1981a) and from healthy donors (Pember et al., 1982) by cation-exchange chromatography. One of the forms required cctyltrimethylammonium bromide (Cetab) for extraction, and a variable distribution was seen in the high-density and low-density azurophilic granules as well as differences in degranulation (Kinkade et al., 1983; Pember & Kinkade, 1983; Olsen & Little, 1984). Differences were also found in enzyme activity and inhibition-sensitivity towards 3-amino-1,24-triazole (Pember al., 1983). However, since the absorption ratios (A/A) and specific enzyme activities indicate enzyme impurity, the interpretation of these differences was in doubt.

Myeloperoxidase (MPO, EC. 1.11.1.7) is an enzyme of the oxidoreductase class that catalyzes the reaction $H_2O_2 + Cl \rightarrow H_2O + OCl$. The enzyme is a hemoprotein found in the azurophil granules of neutrophils and mononuclear phagocytes. The reaction produces hypochlorites with potent antimicrobial activity. It has been reported that the hypochlorite product rather than the hydroxyl radicals is involved in reactive oxygen metabolites (ROM)-mediated injury. And ROM have been implicated in many inflammatory disorders including inflammatory bowel disease (IBD). Drugs such as aminosalicylic acid and sulfasalazine have been shown to scavenge OH, OCl, superoxide as well as inhibit MPO and ameliorate inflammatory diseases.

MPO Assay Procedure

Myeloperoxidase (MPO) isolated from human polymorphonuclear leukocytes (Calbiochem, Cat. No 475911) is used. Test compound and/or vehicle is pre-incubated with 0.02 µg enzyme and 0.0085% hexadecyltrimethylammonium bromide in 100 mM potassium phosphate buffer pH 7.4 for 30 minutes at 25° C. The reaction is then initiated by addition of 1 mM guaiacol as substrate plus 0.15% H2O2 and run for another 5 minutes. The formation of tetraguaiacol is measured by the increase in absorbance at 450 nm. Compounds are screened at 10 µM.

Reference Data—MPO Assay

| Compound | IC50 (µM) |
|---|---|
| *NDGA (Nordihydroguaretic Acid) | 1.0 |

*Indicates standard reference agent used References: Svensson, B. E., Domeij, K., Lindvall, S. and Rydekk, G. Peroxidase and peroxidase-oxidase activities of isolated human myeloperoxidase. Biochem. J. 242: 673–680, 1987.

Example 6

Wound Healing

A patient is suffering from a wound in need of healing. The patient may be administered before, during or after the wounding process, an effective amount of a compound of the present invention. It is expected that after the treatment, the patient's wound would heal more quickly and more effectively, with a decreased change of incomplete wound healing.

Example 7

Diabetic Neuropathy

A patient is suffering from diabetes. A patient may be administered an effective amount of a compound of the present invention. It is expected that, after the treatment, the patient would be neuroprotected to a statistically significant extent and would be less likely to experience diabetic retinopathy than if the patient were not so treated.

Example 8

Inflammation

A patient is suffering from inflammation due to injury or disease. The patient may be administered before, during or after the inflammation, an effective amount of the compound of the present invention. It is expected that after the treatment, the patient's inflammation would be ameliorated more quickly and more effectively.

The invention being thus described, it will be obvious that the same may be varied in many ways. Such variations are not to be regarded as a departure from the spirit and scope of the invention and all such modifications are intended to be included within the scope of the following claims.

We claim:

1. A method of treating an allergy in a mammal, which comprises administering an effective amount of a NAALADase inhibitor to the mammal in need of such treatment.

2. A method of treating an inflammatory disease due to injury in a mammal, which comprises administering an effective amount of a NAALADase inhibitor to the mammal in need of such treatment.

3. The method of claim 2, wherein the NAALADase inhibitor is a compound of formula I

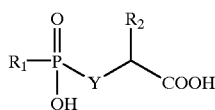

or a pharmaceutically acceptable equivalent, wherein:
Y is $CR_3R_4$, $NR_5$ or O;
$R_1$ is selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl, Ar, COOR, $NR_6R_7$ and OR, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, COOR, $NR_6R_7$ and Ar;
$R_2$ is selected from the group consisting of hydrogen, $C_1$–$C_6$ alkyl, $C_2$–$C_6$ alkenyl, $C_3$–$C_8$ cycloalkyl, $C_5$–$C_7$ cycloalkenyl, Ar, halo and carboxy, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_2$–$C_9$ alkoxy, $C_2$–$C_9$ alkenyloxy, phenoxy, benzyloxy, $NR_6R_7$ and Ar;
$R_3$ and $R_4$ are independently hydrogen or $C_1$–$C_3$ alkyl;
$R_5$ is hydrogen or $C_1$–$C_3$ alkyl;
R, $R_6$ and $R_7$ are independently selected from the group consisting of hydrogen, $C_1$–$C_9$ alkyl, $C_2$–$C_9$ alkenyl, $C_3$–$C_8$-cycloalkyl, $C_5$–$C_7$ cycloalkenyl and Ar, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy and Ar; and
Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl and phenyl, wherein said Ar is unsubstituted or substituted with one or more substituent(s) independently selected from the group consisting of halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, carboxy and amino.

4. The method of claim 3, wherein:
Y is $CH_2$; and
$R_2$ is —$(CH_2)_2COOH$.

5. The method of claim 4, wherein the compound of formula I is selected from the group consisting of:
2-(phosphonomethyl)pentanedioic acid;
2-[[(2-carboxyethyl)hydroxyphosphinyl]methyl] pentanedioic acid;
2-[(benzylhydroxyphosphinyl)methyl]pentanedioic acid;
2-[(benzylhydroxyphosphinyl)methyl]pentanedioic acid;
2-[[((hydroxy)phenylmethyl)hydroxyphosphinyl] methyl]-pentanedioic acid;
2-[(butylhydroxyphosphinyl)methyl]pentanedioic acid;
2-[[(3-methylbenzyl)hydroxyphosphinyl]methyl] pentanedioic acid;
2-[(3-phenylpropylhydroxyphosphinyl)methyl] pentanedioic acid;
2-[[(4-fluorophenyl)hydroxyphosphinyl]methyl] pentanedioic acid;
2-[(methylhydroxyphosphinyl)methyl]pentanedioic acid;
2-[phenylethylhydroxyphosphinyl)methyl]pentanedioic acid;
2-[[(4-methylbenzyl)hydroxyphosphinyl]methyl] pentanedioic acid;
2-[[(4-fluorobenzyl)hydroxyphosphinyl]methyl] pentanedioic acid;
2-[[(4-methoxybenzyl)hydroxyphosphinyl]methyl] pentanedioic acid;
2-[[(3-trifluoromethylbenzyl)hydroxyphosphinyl] methyl]-pentanedioic acid;
2-[[4-trifluoromethylbenzyl)hydroxyphosphinyl]methyl]-pentanedioic acid;
2-[[(2-fluorobenzyl)hydroxyphosphinyl]methyl] pentanedioic acid;
2-[[(2,3,4,5,6-pentafluorobenzyl)hydroxyphosphinyl] methyl]pentanedioic acid; and
pharmaceutically acceptable equivalents.

6. The method of claim 2, wherein the NAALADase inhibitor is a compound of formula II

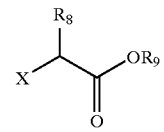

or a pharmaceutically acceptable equivalent, wherein:
X is a moiety of formula (III), (IV) or (V)

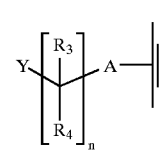

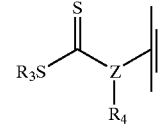

-continued

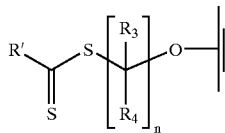
(V)

m and n are independently 0, 1, 2, 3 or 4;

Z is $SR_{13}$, $SO_3R_{13}$, $SO_2R_{13}$, $SOR_{13}$, $SO(NR_{13})R_{14}$ or $S(N_2R_{13}R_{14})R_{15}$;

B is N or $CR_{16}$;

A is O, S, $CR_{17}R_{18}$ or $(CR_{17}R_{18})_mS$;

$R_8$, $R_9$, $R_{10}$, $R_{11}$, $R_{12}$, $R_{13}$, $R_{14}$, $R_{15}$, $R_{16}$, $R_{17}$ and R is are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula (III) and A is O, then n is 2,3 or 4; when X is a moiety of formula (III) and A is S, then n is 2, 3 or 4; and when X is a moiety of formula (III) and A is $(CR_{17}R_{18})_mS$, then n is 0, 2, 3 or 4.

7. The method of claim 6, wherein X is a moiety of formula (III).

8. The method of claim 7, wherein:

n is 0, 1, 2 or 3;

Z is SH;

A is O, S, or $CR_{17}R_{18}$; and $R_8$ is —$(CH_2)_2COOH$.

9. The method of claim 8, wherein the compound of formula II is selected from the group consisting of:

2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

10. The method of claim 6, wherein the compound of formula II is an enantiomer or an enantiomer-enriched mixture.

11. The method of claim 6, wherein the NAALADase inhibitor is a compound of formula I

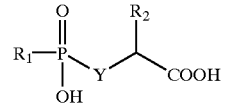
I or a pharmaceutically acceptable equivalent, wherein:

Y is $CR_3R_4$, $NR_5$ or O;

$R_1$ is selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl, Ar, COOR, $NR_6R_7$ and OR, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy, COOR, $NR_6R_7$ and Ar;

$R_2$ is selected from the group consisting of hydrogen, $C_1$–$C_6$ alkyl, $C_2C_6$ alkenyl, $C_3$–$C_8$ cycloalkyl, $C_5$–$C_7$ cycloalkenyl, Ar, halo and carboxy, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1C_6$ alkyl, $C_2$–$C_6$ alkenyl, $C_1$–$C_9$ alkoxy, $C_2$–$C_9$ alkenyloxy, phenoxy, benzyloxy, $NR_6R_7$ and Ar;

$R_3$ and $R_4$ are independently hydrogen or $C_1$–$C_3$ alkyl;

$R_5$ is hydrogen or $C_1$–$C_3$ alkyl;

R, $R_6$ and $R_7$ are independently selected from the group consisting of hydrogen, $C_1$–$C_9$ alkyl, $C_2$–$C_9$ alkenyl, $C_3$–$C_8$ cycloalkyl, $C_5$–$C_7$ cycloalkenyl and Ar, wherein said alkyl, alkenyl, cycloalkyl and cycloalkenyl are unsubstituted or substituted with one or more substituent(s) independently selected from the group consisting of carboxy, $C_3$–$C_8$ cycloalkyl, $C_5$–$C_7$ cycloalkenyl, halo, hydroxy, nitro, trifluoromethyl, $C_1$–$C_6$ alkyl, $C_2$–$C_6$ alkenyl, $C_1$–$C_9$ alkoxy, $C_2$–$C_9$ alkenyloxy, phenoxy, benzyloxy and Ar; and Ar is selected from the group consisting of 1-naphthyl, 2-naphthyl, 2-indolyl, 3-indolyl, 4-indolyl, 2-furyl, 3-furyl, tetrahydrofuranyl, tetrahydropyranyl, 2-thienyl, 3-thienyl, 2-pyridyl, 3-pyridyl, 4-pyridyl and phenyl, wherein said Ar is unsubstituted or substituted with one or more substituent(s) independently selected from the group consisting of halo, hydroxy, nitro, trifluoromethyl, $C_1$–$C_6$ alkyl, $C_2$–$C_6$ alkenyl, $C_1$–$C_6$ alkoxy, $C_2$–$C_6$ alkenyloxy, phenoxy, benzyloxy, carboxy and amino.

12. The method of claim 11, wherein:

Y is $CH_2$; and $R_2$ is —$(CH_2)_2COOH$.

13. The method of claim 12, wherein of formula I is selected from the group consisting of:

2-(phosphonomethyl)pentanedioic acid;
2-[[(2-carboxyethyl)hydroxyphosphinyl]methyl]pentanedioic acid;
2-[(benzylhydroxyphosphinyl)methyl]pentanedioic acid;
2-[(benzylhydroxyphosphinyl)methyl]pentanedioic acid;
2-[[((hydroxy)phenylmethyl)hydroxyphosphinyl]methyl]-pentanedioic acid;

2-[(butylhydroxyphosphinyl)methyl]pentanedioic acid;
2-[[(3-methylbenzyl)hydroxyphosphinyl]methyl]pentanedioic acid;
2-[(3-phenylpropylhydroxyphosphinyl)methyl]pentanedioic acid;
2-[[(4-fluorophenyl)hydroxyphosphinyl]methyl]pentanedioic acid;
2-[(methylhydroxyphosphinyl)methyl]pentanedioic acid;
2-[phenylethylhydroxyphosphinyl)methyl]pentanedioic acid;
2-[[(4-methylbenzyl)hydroxyphosphinyl]methyl]pentanedioic acid;
2-[[(4-fluorobenzyl)hydroxyphosphinyl]methyl]pentanedioic acid;
2-[[(4-methoxybenzyl)hydroxyphosphinyl]methyl]pentanedioic acid;
2-[[(3-trifluoromethylbenzyl)hydroxyphosphinyl]methyl]-pentanedioic acid;
2-[[4-trifluoromethylbenzyl)hydroxyphosphinyl]methyl]-pentanedioic acid;
2-[[(2-fluorobenzyl)hydroxyphosphinyl]methyl]pentanedioic acid;
2-[[(2,3,4,5,6-pentafluorobenzyl)hydroxyphosphinyl]methyl]pentanedioic acid; and
pharmaceutically acceptable equivalents.

14. The method of claim 1, wherein the NAALADase inhibitor is a compound of formula II

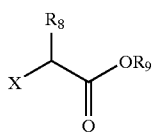

II or a pharmaceutically acceptable equivalent, wherein:
X is a moiety of formula (III), (IV) or (V)

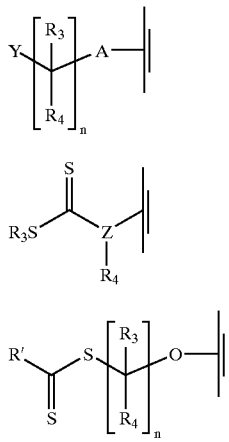

m and n are independently 0, 1, 2, 3 or 4;
Z is $SR_{13}$, $SO_3R_{13}$, $SO_2R_{13}$, $SOR_{13}$, $SO(NR_{13})R_{14}$ or $S(N_2R_{13}R_{14})R_{15}$;

B is N or $CR_{16}$;
A is O, S, $CR_{17}R_{15}$ or $(CR_{17}R_{18})_mS$;
$R_8$, $R_9$, $R_{10}$, $R_{11}$, $R_{12}$, $R_{13}$, $R_{14}$, $R_{15}$, $R_{16}$, $R_{17}$ and $R_{18}$ are independently hydrogen, $C_1$–$C_9$ straight or branched chain alkyl, $C_2$–$C_9$ straight or branched chain alkenyl, $C_3$–$C_8$ cycloalkyl, $C_5$–$C_7$ cycloalkenyl, $Ar_1$, hydroxy, carboxy, carbonyl, amino, amido, cyano, isocyano, nitro, sulfonyl, sulfoxy, thio, thiocarbonyl, thiocyano, formanilido, thioformamido, sulfhydryl, halo, haloalkyl, trifluoromethyl or oxy, wherein said alkyl, alkenyl, cycloalkyl and cycloalkenyl are independently unsubstituted or substituted with one or more substituent(s); and $Ar_1$ is a carbocyclic or heterocyclic moiety, which is unsubstituted or substituted with one or more substituent(s);

provided that when X is a moiety of formula (III) and A is O, then n is 2, 3 or 4; when X is a moiety of formula (III) and A is S, then n is 2, 3 or 4; and when X is a moiety of formula (III) and A is $(CR_{17}R_{18})_mS$, then n is 0, 2, 3 or 4.

15. The method of claim 14, wherein X is a moiety of formula (III).

16. The method of claim 15, wherein:
n is 0, 1, 2 or 3;
Z is SH;
A is O, S, or $CR_{17}R_{18}$; and
$R_8$ is —$(CH_2)_2COOH$.

17. The method of claim 16, wherein the compound of formula II is selected from the group consisting of:
2-(2-sulfanylethyl)pentanedioic acid;
3-(2-sulfanylethyl)-1,3,5-pentanetricarboxylic acid;
2-(2-sulfanylpropyl)pentanedioic acid;
2-(2-sulfanylbutyl)pentanedioic acid;
2-(2-sulfanyl-2-phenylethyl)pentanedioic acid;
2-(2-sulfanylhexyl)pentanedioic acid;
2-(2-sulfanyl-1-methylethyl)pentanedioic acid;
2-[1-(sulfanylmethyl)propyl]pentanedioic acid;
2-(3-sulfanylpentyl)pentanedioic acid;
2-(3-sulfanylpropyl)pentanedioic acid;
2-(3-sulfanyl-2-methylpropyl)pentanedioic acid;
2-(3-sulfanyl-2-phenylpropyl)pentanedioic acid;
2-(3-sulfanylbutyl)pentanedioic acid;
2-[3-sulfanyl-2-(phenylmethyl)propyl]pentanedioic acid;
2-[2-(sulfanylmethyl)butyl]pentanedioic acid;
2-[2-(sulfanylmethyl)pentyl]pentanedioic acid;
2-(3-sulfanyl-4-methylpentyl)pentanedioic acid; and
pharmaceutically acceptable equivalents.

18. The method of claim 14, wherein the compound of formula II is an enantiomer or an enantiomer-enriched mixture.

* * * * *